US009883865B2

(12) United States Patent
Freyman et al.

(10) Patent No.: US 9,883,865 B2
(45) Date of Patent: Feb. 6, 2018

(54) IN-SITU FORMING FOAMS WITH OUTER LAYER

(71) Applicant: ARSENAL MEDICAL, INC., Watertown, MA (US)

(72) Inventors: Toby Freyman, Waltham, MA (US); Joseph Lomakin, Cambridge, MA (US); John Marini, Weymouth, MA (US); Jennifer Mortensen, Somerville, MA (US); Adam Rago, Falmouth, MA (US); Rany Busold, Medford, MA (US); Upma Sharma, Somerville, MA (US); Gregory T. Zugates, Chelmsford, MA (US)

(73) Assignee: ARSENAL MEDICAL, INC., Watertown, MA (US)

( * ) Notice: Subject to any disclaimer, the term of this patent is extended or adjusted under 35 U.S.C. 154(b) by 0 days.

(21) Appl. No.: 14/728,393

(22) Filed: Jun. 2, 2015

(65) Prior Publication Data

US 2016/0051264 A1    Feb. 25, 2016

Related U.S. Application Data

(63) Continuation of application No. 13/815,910, filed on Mar. 15, 2013, now Pat. No. 9,044,580, which is a
(Continued)

(51) Int. Cl.
*A61F 2/06* (2013.01)
*A61B 17/12* (2006.01)
*A61M 37/00* (2006.01)
*A61L 31/06* (2006.01)
*A61L 31/12* (2006.01)
*A61L 31/14* (2006.01)
*A61L 24/00* (2006.01)
(Continued)

(52) U.S. Cl.
CPC .... *A61B 17/12181* (2013.01); *A61B 17/1214* (2013.01); *A61B 17/12113* (2013.01);
(Continued)

(58) Field of Classification Search
CPC .... A61F 2/02; A61F 2/06; A61F 2/07; A61M 37/00; A61L 31/06; A61L 31/128
See application file for complete search history.

(56) References Cited

U.S. PATENT DOCUMENTS 4,243,755 A    1/1981   Marx et al.
4,764,377 A    8/1988   Goodson
(Continued)

FOREIGN PATENT DOCUMENTS

WO    WO-1994/18956 A1    9/1994
WO    WO-2003/020161 A2   3/2003
(Continued)

OTHER PUBLICATIONS

Rhee et al, "Treatment of type II endoleaks with a novel polyurethane thrombogenic foam; Induction of endoleak thrombosis and elimination of intra-aneurysmal pressure in the canine model" *Journal of Vascular Studies*, 42:2, 321-328, Aug. 2005.
(Continued)

*Primary Examiner* — Victor Nguyen

(57) ABSTRACT

Systems, methods and kits relating to in-situ forming polymer foams for the treatment of aneurysms or fluid filled spaces are disclosed. The systems include an insertable medical device and an in-situ forming foam of lava like materials with a fast forming outer skin and a slower hardening interior that is formed from a one-, two- or multi-part formulation. When used to treat an aneurysm, the foam is placed into contact with at least a portion of an exterior surface of the medical device and/or the tissue surface of the aneurysm.

9 Claims, 8 Drawing Sheets

Related U.S. Application Data continuation-in-part of application No. 13/209,020, filed on Aug. 12, 2011, now Pat. No. 9,173,817, and a continuation-in-part of application No. 12/862,362, filed on Aug. 24, 2010.

(60) Provisional application No. 61/236,314, filed on Aug. 24, 2009.

(51) Int. Cl.
*A61L 24/04* (2006.01)
*A61F 2/07* (2013.01)
*A61J 1/20* (2006.01)

(52) U.S. Cl.
CPC .......... *A61B 17/12118* (2013.01); *A61F 2/07* (2013.01); *A61L 24/0036* (2013.01); *A61L 24/0089* (2013.01); *A61L 24/046* (2013.01); *A61L 31/06* (2013.01); *A61L 31/128* (2013.01); *A61L 31/146* (2013.01); *A61M 37/00* (2013.01); *A61B 2017/1205* (2013.01); *A61F 2002/065* (2013.01); *A61F 2002/077* (2013.01); *A61F 2210/0085* (2013.01); *A61J 1/2093* (2013.01); *A61L 2300/60* (2013.01); *A61L 2400/06* (2013.01)

(56) References Cited

U.S. PATENT DOCUMENTS

| | | | |
|---|---|---|---|
| 5,364,627 A | 11/1994 | Song | |
| 5,538,735 A | 7/1996 | Ahn | |
| 5,567,612 A | 10/1996 | Vacanti et al. | |
| 5,569,528 A | 10/1996 | Van der Loo et al. | |
| 5,725,568 A | 3/1998 | Hastings | |
| 5,800,476 A | 9/1998 | Piunti | |
| 5,842,477 A | 12/1998 | Naughton et al. | |
| 5,922,340 A | 7/1999 | Berde et al. | |
| 5,944,341 A | 8/1999 | Kimura et al. | |
| 5,980,927 A | 11/1999 | Nelson et al. | |
| 6,002,968 A | 12/1999 | Edwards | |
| 6,086,911 A | 7/2000 | Godbey | |
| 6,156,842 A | 12/2000 | Hoenig et al. | |
| 6,211,259 B1 | 4/2001 | Borden et al. | |
| 6,214,370 B1 | 4/2001 | Nelson et al. | |
| 6,382,526 B1 | 5/2002 | Reneker et al. | |
| 6,495,124 B1 | 12/2002 | Samour | |
| 6,520,425 B1 | 2/2003 | Reneker | |
| 6,524,608 B2 | 2/2003 | Ottoboni et al. | |
| 6,596,296 B1 | 7/2003 | Nelson et al. | |
| 6,655,366 B2 | 12/2003 | Sakai | |
| 6,676,953 B2 | 1/2004 | Hexamer | |
| 6,676,960 B2 | 1/2004 | Saito et al. | |
| 6,685,956 B2 | 2/2004 | Chu et al. | |
| 6,685,957 B1 | 2/2004 | Bezemer et al. | |
| 6,689,374 B2 | 2/2004 | Chu et al. | |
| 6,695,992 B2 | 2/2004 | Reneker | |
| 6,712,610 B2 | 3/2004 | Abdennour et al. | |
| 6,716,449 B2 | 4/2004 | Oshlack et al. | |
| 6,737,447 B1 | 5/2004 | Smith et al. | |
| 6,753,454 B1 | 6/2004 | Smith et al. | |
| 6,821,479 B1 | 11/2004 | Smith et al. | |
| 6,855,366 B2 | 2/2005 | Smith et al. | |
| 6,858,222 B2 | 2/2005 | Nelson et al. | |
| 6,861,142 B1 | 3/2005 | Wilkie et al. | |
| 6,861,570 B1 | 3/2005 | Flick | |
| 6,913,760 B2 | 7/2005 | Carr et al. | |
| 7,029,495 B2 | 4/2006 | Stinson | |
| 7,033,603 B2 | 4/2006 | Nelson et al. | |
| 7,033,605 B2 | 4/2006 | Wong | |
| 7,048,913 B2 | 5/2006 | Hexamer | |
| 7,048,946 B1 | 5/2006 | Wong et al. | |
| 7,074,392 B1 | 7/2006 | Friedman et al. | |
| 7,135,194 B2 | 11/2006 | Birnbaum | |
| 7,172,765 B2 | 2/2007 | Chu et al. | |
| 7,198,794 B1 | 4/2007 | Riley | |
| 7,214,506 B2 | 5/2007 | Tatsumi et al. | |
| 7,235,295 B2 | 6/2007 | Laurencin et al. | |
| 7,285,266 B2 | 10/2007 | Vournakis et al. | |
| 7,309,498 B2 | 12/2007 | Belenkaya et al. | |
| 7,323,190 B2 | 1/2008 | Chu et al. | |
| 7,462,362 B2 | 12/2008 | Kepka et al. | |
| 7,678,366 B2 | 3/2010 | Friedman et al. | |
| 7,737,060 B2 | 6/2010 | Strickler et al. | |
| 7,765,647 B2 | 8/2010 | Smith et al. | |
| 7,799,965 B2 | 9/2010 | Patel et al. | |
| 7,803,395 B2 | 9/2010 | Datta et al. | |
| 7,815,928 B2 | 10/2010 | Cherif Cheikh | |
| 7,824,699 B2 | 11/2010 | Ralph et al. | |
| 7,959,616 B2 | 6/2011 | Choi et al. | |
| 7,959,848 B2 | 6/2011 | Reneker et al. | |
| 7,959,904 B2 | 6/2011 | Repka | |
| 7,997,054 B2 | 8/2011 | Bertsch et al. | |
| 9,044,580 B2 * | 6/2015 | Freyman | A61L 31/06 |
| 2001/0021873 A1 | 9/2001 | Stinson | |
| 2002/0165582 A1 | 11/2002 | Porter | |
| 2002/0176893 A1 | 11/2002 | Wironen et al. | |
| 2003/0017208 A1 | 1/2003 | Ignatious et al. | |
| 2003/0068353 A1 | 4/2003 | Chen et al. | |
| 2003/0171773 A1 | 9/2003 | Carrison | |
| 2003/0195611 A1 | 10/2003 | Greenhalgh et al. | |
| 2004/0030377 A1 | 2/2004 | Dubson et al. | |
| 2004/0034408 A1 | 2/2004 | Majercak et al. | |
| 2004/0049002 A1 | 3/2004 | Andrews et al. | |
| 2004/0076661 A1 | 4/2004 | Chu et al. | |
| 2004/0217503 A1 | 11/2004 | Grinshpun et al. | |
| 2005/0033163 A1 | 2/2005 | Duchon et al. | |
| 2005/0042293 A1 | 2/2005 | Jackson et al. | |
| 2005/0106211 A1 | 5/2005 | Nelson et al. | |
| 2005/0165480 A1 * | 7/2005 | Jordan | A61B 17/12022 623/9 |
| 2005/0175662 A1 * | 8/2005 | Hunter | A61B 17/12022 424/423 |
| 2005/0276841 A1 | 12/2005 | Davis et al. | |
| 2006/0008419 A1 | 1/2006 | Hissink et al. | |
| 2006/0153815 A1 | 7/2006 | Seyda et al. | |
| 2006/0276831 A1 | 12/2006 | Porter et al. | |
| 2006/0293743 A1 | 12/2006 | Andersen et al. | |
| 2007/0005140 A1 | 1/2007 | Kim et al. | |
| 2007/0087027 A1 | 4/2007 | Greenhalgh et al. | |
| 2007/0155273 A1 | 7/2007 | Chu et al. | |
| 2007/0176333 A1 | 8/2007 | Greene et al. | |
| 2007/0232169 A1 | 10/2007 | Strickler et al. | |
| 2007/0293297 A1 | 12/2007 | Schugar | |
| 2008/0053891 A1 | 3/2008 | Koops et al. | |
| 2008/0132936 A1 | 6/2008 | Sawhney et al. | |
| 2008/0245371 A1 | 10/2008 | Gruber | |
| 2008/0264423 A1 | 10/2008 | Duchon et al. | |
| 2008/0269126 A1 | 10/2008 | Ballance et al. | |
| 2008/0281350 A1 | 11/2008 | Sepetka et al. | |
| 2009/0155326 A1 | 6/2009 | Mack et al. | |
| 2010/0076484 A1 | 3/2010 | Riina et al. | |
| 2010/0131002 A1 | 5/2010 | Connor et al. | |
| 2010/0249913 A1 | 9/2010 | Datta et al. | |
| 2010/0291182 A1 | 11/2010 | Palasis et al. | |
| 2010/0318108 A1 | 12/2010 | Datta et al. | |
| 2011/0184530 A1 | 7/2011 | Datta et al. | |
| 2011/0237994 A1 | 9/2011 | Russ et al. | |
| 2012/0107439 A1 | 5/2012 | Sharma et al. | |
| 2012/0197284 A1 | 8/2012 | Ogle et al. | |

FOREIGN PATENT DOCUMENTS

| | | | |
|---|---|---|---|
| WO | WO-2007/052042 A2 | 5/2007 | |
| WO | WO-2008/013713 A2 | 1/2008 | |
| WO | WO 2011/007352 | 1/2011 | |
| WO | 2014004160 A1 | 1/2014 | |

OTHER PUBLICATIONS

Kanani et al., "Review on Electrospul Nanofibers Scaffold and Biomedical Applications", Trends Biomater, Artif, Organs, vol. 24(2), pp. 93-115, (Aug. 2010).

(56) References Cited

OTHER PUBLICATIONS

Biomedical Structures, Glossary: Common Biomedical Textile Terms (accessed Oct. 12, 2011), 1-11 pgs.
Bini, T.B. et al., "Electrospun poly(L-lactide-co-glycolide) biodegradable polymer nanofiber tubes for peripheral nerve regeneration", Nanotechnology, 15, 2004, 1459-1464.
Jose, Moncy V. et al., "Fabrication and characterization of aligned nanofibrous FLGA/Collagen blends as bone tissue scaffolds", Polymer, 50, 2009, 3778-3785.
Liao, Yiliang et al., "Preparation, characterization, and encapsulation/release studies of a composite nanofiber mat electrospun from an emulsion containing poly(lactic-co-glycolic acid)", Polymer, 49, 2008, 5294-5299.
Wei, Kai et al., "Emulsion Electrospinning of a Collegen-like Protein/PLGA Fibrous Scaffold: Empirical Modeling and Preliminary Release Assessment of Encapsulated Protein", Macromolecular Bioscience, 11, 2011, 1526-1536.
Sy, Jay C. et al., "Emulsion as a Menas of Controlling Electrospinning of Polymers", Advanced Materials, 21, 2009, 1814-1819.
International Search Report dated Jan. 18, 2011 for International Application No. PCT/US2010/057010 (3pgs).
International Search Report dated Jan. 5, 2012 for International Application No. PCT/US2011/47615 (3 pgs).
International Search Report dated Jan. 2, 2013 for International Application No. PCT/US2012/062732.
International Search Report dated Jun. 18, 2013 for International Application No. PCT/US2013/046281 (4 pgs).

\* cited by examiner

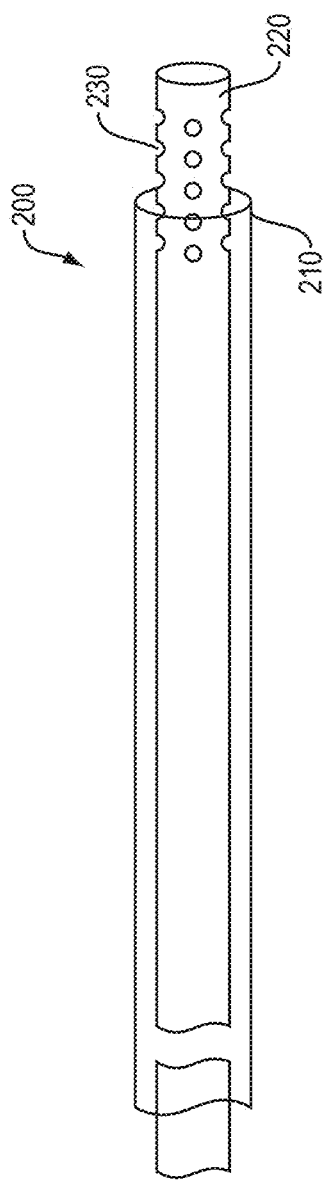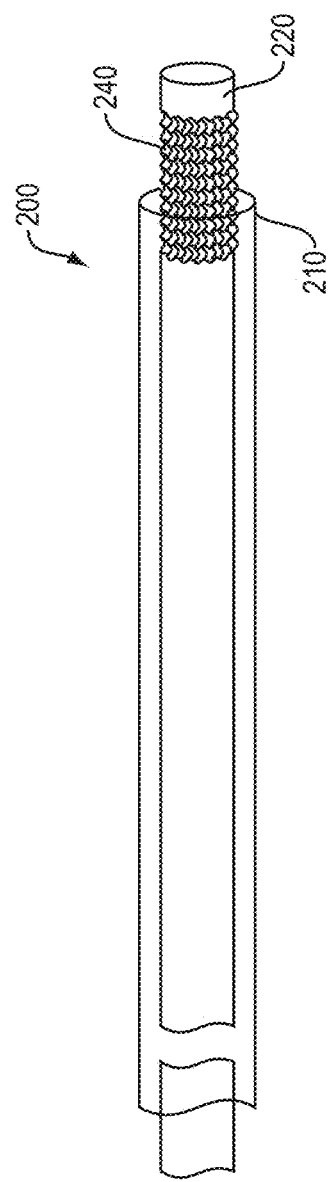

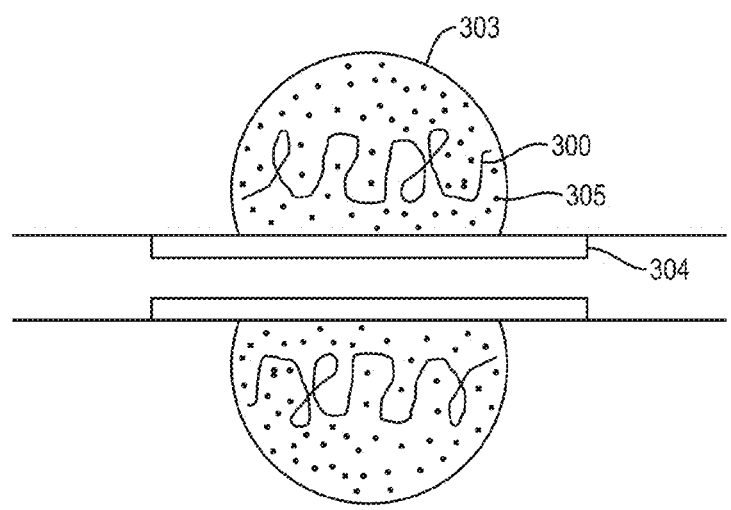
FIG. 6
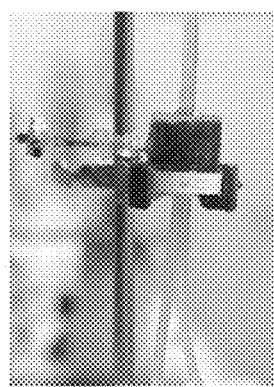 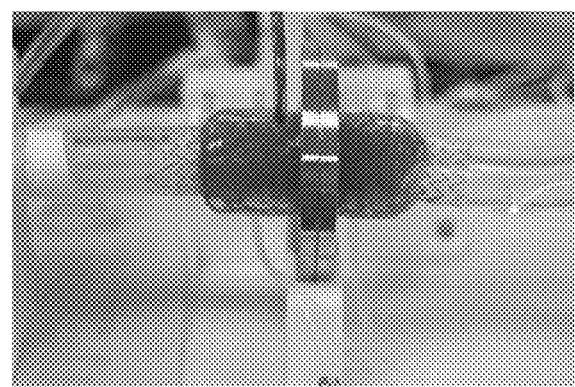
FIG. 7A  FIG. 7B

IN-SITU FORMING FOAMS WITH OUTER LAYER

CROSS-REFERENCE TO RELATED APPLICATIONS

This application is a Continuation of U.S. application Ser. No. 13/815,910, filed Mar. 15, 2013, now U.S. Pat. No. 9,044,580, which Issued on Jun. 2, 2015. This application is a continuation-in-part of U.S. application Ser. No. 13/209,020, filed Aug. 12, 2011 and titled "In-situ Forming Hemostatic Foam Implants," which is a continuation-in-part of U.S. application Ser. No. 12/862,362, filed Aug. 24, 2010 and titled "Systems and Methods Relating to Polymer Foams," which claims priority to U.S. Provisional Patent Application Ser. No. 61/236,314 filed Aug. 24, 2009, titled "Systems and Methods Relating to Polymer Foams," each of which is incorporated by reference herein for all purposes.

FIELD OF INVENTION

Systems and methods relating to polymer foams for the treatment of aneurysms and other body cavities are generally described.

BACKGROUND

Controlling fluid, gas or material movement in the body has numerous clinical applications and benefits, including controlling hemorrhage, preventing aneurysm growth or risk of rupture, treating tumors and managing respiratory disorders. These treatments often require introduction of a material to fill or partially fill a space, potential space, vessel, cavity or other volume inside and/or on the surface of the body. However, it can be appreciated that movement of that material outside the targeted treatment zone could have undesirable effects, cause complications, limit efficacy or lead to morbidity or mortality.

In one clinical application in which polymers or other materials have been used to control movement of bodily fluids is in the treatment of aneurysms. Generally, an aneurysm is an abnormal widening or ballooning of a portion of a blood vessel due to weakness in the vessel wall. If left untreated, aneurysms can grow large and rupture, causing internal bleeding which is often fatal. Two locations in which aneurysms are commonly found are in the abdominal aorta and the brain.

Abdominal aortic aneurysms ("AAAs") are conventionally treated by surgical repair/removal or by endovascular repair. If the AAA is surgically repaired, a major incision is made in the abdomen or chest to access and remove and/or repair the aneurysm, and the aneurysmal segment of aorta is replaced or supplemented with a tubular graft of synthetic material such as Dacron® or Teflon®. If instead it is treated by endovascular aneurysm repair ("EVAR"), the AAA is accessed via catheter using minimally invasive techniques rather than through an open surgical incision. A graft or stent-graft is delivered through the catheter and self-expands as it is expelled from the catheter to bridge the aneurysm to form a stable channel for blood flow. FIG. 1 shows an aneurysm 110 in an abdominal aorta 115 after treatment by the placement of a stent-graft 150, as is known in the art. With the increased use of EVAR in recent years, a higher incidence of endoleaks has been observed. An endoleak results from blood that is still able to access the aneurysm sac 116 after placement of the graft or stent-graft. Such a leak could be caused by an insufficient seal at the ends of the graft (referred to as a "type I" leak), retrograde flow into the aneurysm from collateral vessels (a "type II" leak), a defect in the graft (a "type III" leak), and flow through any porosity in the graft (a "type IV" leak). Such endoleaks represent a significant possible drawback to EVAR procedures as they could lead to aneurysm expansion or rupture. Endoleaks are less of a concern following surgical repair of AAA, but the surgical procedure is significantly more invasive and has higher mortality and morbidity. Thus, an improved EVAR device and system which address endoleaks would provide a significant improvement in patient care.

It has recently been proposed (Rhee et al., "Treatment of type II endoleaks with a novel polyurethane thrombogenic foam: Induction of endoleak thrombosis and elimination of intra-aneurysmal pressure in the canine model," *J. Vasular Surgery* 2005, 42(2): 321-8), incorporated herein by reference, to use a pre-formed polyurethane foam in the aneurysm sac following an EVAR procedure. The authors found that the use of such a foam resulted in a reduction of intra-aneurysmal pressure to a level that was indistinguishable from control aneurysms that had no endoleak. Such a pre-formed foam, however, cannot be shaped in-situ to conform to the configuration of the aneurysm sac. As such, the authors were required to make use of numerous foam implants to achieve the reported results.

Likewise, it has been proposed in U.S. Publication No. 2009/0287145, incorporated herein by reference, to introduce a foam material into an aneurysm. The foam is compressible to allow for injection and then expands from its compressed configuration and hardens in-situ. The foam itself, however, is pre-formed prior to injection into the aneurysm.

SUMMARY OF THE INVENTION

Systems, methods and kits relating to in-situ forming polymer foams for the treatment of aneurysms or other body cavities are provided.

In one aspect, the present invention relates to a method for treating an aneurysm within a patient, the aneurysm characterized by a first end, a second end, and a tissue surface between the first and second ends. The method comprises the steps of placing a medical device having an exterior surface within the aneurysm; and forming an in-situ forming foam between the exterior surface of the medical device and the tissue surface of the aneurysm. The in-situ forming foam comprises a polymer that reacts in-situ to generate a gas and form a foam structure comprising a first portion comprising a skin and a second portion within said first portion. The foam is formed from a one-part, two-part, or multi-part formulation, as defined herein.

In another aspect, the present invention comprises a system comprising an insertable medical device and an in-situ forming foam. The medical device comprises a structure having a first end, a second end, and an exterior surface between the first and second ends. The in-situ forming foam comprises a polymer that reacts in-situ to generate a gas and form a foam structure comprising a first portion comprising a skin and a second portion within said first portion. The system optionally includes a delivery catheter for the delivery of the polymer into the space between the exterior surface of the medical device and the tissue surface of the aneurysm.

In another aspect, the present invention comprises a kit that includes a medical device and a polymer formulation. The medical device comprises a structure having a first end, a second end, and an exterior surface between the first and second ends. The polymer formulation reacts in-situ to generate a gas and form a foam with a skin.

In another aspect, the present invention comprises delivery catheters and related methods for the delivery of formulations that are adapted to react in-situ to generate a gas and form a foam with a skin.

In another aspect, the present invention comprises instructions for treating an aneurysm. The instructions instruct a healthcare provider to place a medical device such as a stent-graft within the aneurysm and to insert an in-situ foaming formulation between an exterior surface of the medical device and the tissue surface of the aneurysm, where the in-situ foaming formulation comprises a polymer that reacts in-situ to generate a gas and form a foam with a skin.

In other aspects, the invention includes foams, compositions, formulations, products, kits, and systems that are useful for providing the foams and performing the methods described above.

The present invention offers advantages not previously known in the art. For example, the polymers of the invention can be deployed into an aneurysm sac without requiring specific knowledge of the aneurysm configuration while nonetheless creating conformal contact within the sac and thus minimizing and/or preventing endoleaks and stabilizing pressure within the space. Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 4A and 4B show systems for the delivery of in-situ forming foams, in accordance with embodiments of the present invention.

FIG. 6 shows a cross-sectional view of the present invention in which a coil with an in-situ forming coating has been placed in the space between a stent-graft and an aneurysm sac.

FIGS. 7A and 7B show the formation of lava-like foam from a two-part formulation.

DETAILED DESCRIPTION

Figure 1:
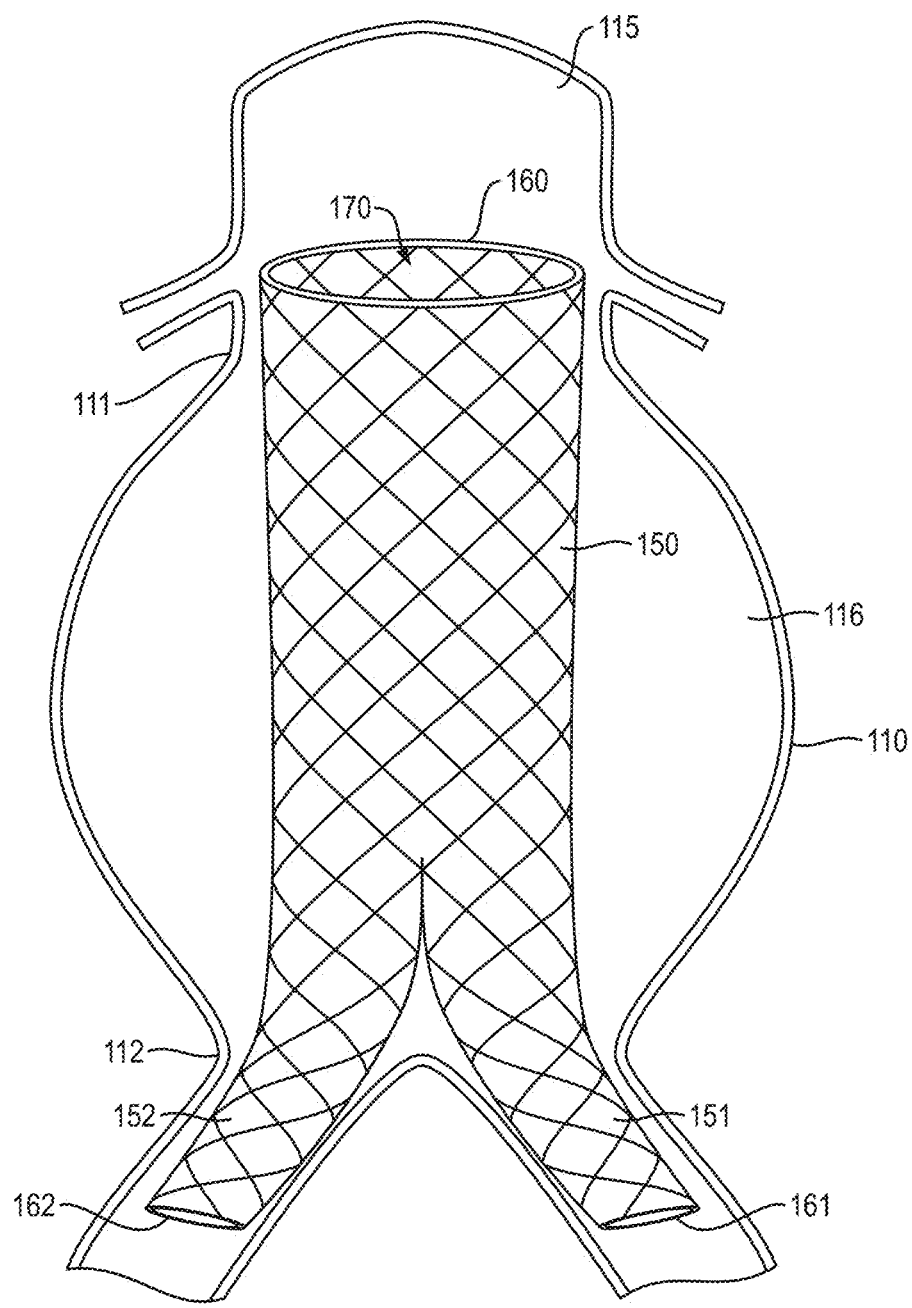
FIG. 1 shows the conventional placement of a stent-graft within an abdominal aortic aneurysm.

Systems, methods and kits related to the treatment of aneurysms using in-situ forming polymer foams are generally described. As will be recognized by those skilled in the art, although the present invention is described with specific reference to the use of in-situ forming foams within aneurysm sacs, the foams of the present invention may be applied to any vessels, organs, tubular structures, lumens, spaces or potential spaces, chambers, appendages, wounds, surgically created volumes, body cavities such as abdominal, pelvic, and cardio thoracic cavities, and placed in contact with, for example, tissue, injured tissue, internal organs, etc. As used herein, "aneurysm sac" refers to the sac formed by the localized dilation in a blood vessel at an aneurysm site. For the purposes of this disclosure, the terms "formulation", "polymer formulation", "polymer material", "prepolymer" and "prepolymer formulation" are used interchangeably to designate a polymer-based system or material capable of further reaction in a vessel or cavity. These terms can refer to a single prepolymer material, or a prepolymer material blended with other additives (e.g., catalysts, surfactants, solvents, diluents, crosslinkers, chain extenders, blowing agents) to create a prepolymer formulation.

The polymer foams of the present invention are formed "in-situ." That is, the foams are formed by the reaction of polymer(s) in-situ simultaneously with, or shortly after, delivery to an aneurysm sac or other bodily cavity. It should be understood that, throughout the description of the present invention, the systems and methods of the present invention are applicable to any suitable bodily cavity notwithstanding that the invention is described with specific reference to the treatment of aneurysms. The polymer(s) react in the presence of an aqueous environment (e.g., blood, water, etc.) or other trigger (e.g., pH, temperature, ion concentration, electrical current, magnetic field or other trigger) in a one-part system and/or react with each other (e.g., for embodiments in which polymer components are delivered separately and either concurrently or sequentially) in a two- or multi-part system upon such delivery. This is in contrast to pre-formed foams, which are formed prior to the time that they are delivered into the body. The foamed polymers of the present invention may be capable of exerting a pressure on an internal surface of an aneurysm sac and thus prevent or limit movement of a bodily fluid (e.g., blood, etc.) and/or prevent or limit endoleaks as previously described. Such in-situ forming foams preferably expand to fill the aneurysm sac volume, resulting in conformal contact with the aneurysm walls and may include penetration into blood vessels and other lumens opening into the sac without clinically undesirable embolization. The location of such vessels is not always obvious with standard imaging technique, such that the ability to seal such vessels with the foams and methods of the present invention without requiring visualization is a unique advantage of the present invention. Also, the foams are formed by the reaction of polymers in-situ to yield gas generation and expansion, which allows for the use of minimal polymer materials to fill the space and allows the resulting foam to push through fluid, including actively flowing blood, to provide conformal contact with surrounding tissue.

In some embodiments, the foam of the present invention is described to be "lava like" in that it is viscous yet flowable and hardens from its exterior surface towards its interior. The external skin of the foam forms as a fast-forming, robust, balloon-like outer layer that encases the polymer formulation, promotes material cohesion, and resists deformation and movement into collateral vessels or outside the targeted area. Formation of the skin occurs in whole or in part due to contact with a trigger in the environment (e.g., water, temperature, blood, etc.), and therefore, as the foam expands and the skin deforms to expose internal formulation, it too will react and reform the skin rapidly. The outer layer may be characterized as a "skin" in some embodiments that have a thin exterior layer that is more hard or solid, or less flowable, than the material contained by the outer layer. Moreover, the skin may be characterized as being "robust" because it has mechanical properties (e.g., strength, toughness, etc.) that are more optimal, at least for some period of time, to the material contained by the skin. The interior of the material hardens more slowly via the same or a secondary process, as compared to the skin. In some cases where the skin forms rapidly and is likely sufficiently robust mechanically, resulting in a continuous, packable polymer, which may tend to form as a coil. Through continued extrusion of the material out of a delivery device such as a catheter or microcatheter, the user can create a long coil to partially or completely fill an aneurysm space or other bodily cavity. The space may be filled with an aneurysm coil or other medical device and an in-situ forming foam or an aneurysm coil or other medical device that is coated with a material that expands to form a foam coating in-situ. The continuous, long aspect ratio of the coil and cured outer surface prevents the coil from entering the collateral vessels to a significant degree, which could lead to adverse events. In addition, some embodiments could be envisioned where the coil diameter expands to a size that is larger than any of the collateral vessel diameters, thus preventing entry into the collateral vessels in the short aspect ratio as well. These and other factors are important distinctions and advantages of in-situ forming foams over systems and methods that make use of pre-formed foams.

The polymer foams of the present invention may possess attributes that make them particularly suitable for use within the body. For example, the foams of the present invention are biocompatible and may be either biodegradable or biostable. In some instances, the polymers may be sufficiently elastic to allow for body movement while being sufficiently stiff to support body tissues and the endovascular graft or associated or similar medical devices. In some embodiments, the composition may be adjusted so that it wets tissues effectively. Furthermore, pendant groups may be attached that allow for the targeted adhesion of polymer to tissues or injured tissues. Functionalization of the polymer used to form the foam may also lead to covalent bonding of the foam to a surface inside the aneurysm sac, which may aid, for example, in preventing dislocation of the foam within the cavity. In addition, the polymers may comprise entities that allow for the degradation of the polymer foam via an external stimulus such as UV radiation, heat, etc. The polymers and/or foams formed therefrom may also be capable of interacting with contrast agents, allowing for the visualization of the foam and/or an aneurysm sac. This interaction may be permanent or temporary. These and other aspects of the foams used in the present invention are more fully described herein.

Examples of in-situ forming foams and methods of using such foams for the treatment of aneurysms are now provided.

FIG. 1 shows the placement of a stent-graft within an abdominal aortic aneurysm, as is known in the art. Although the present invention is described with specific reference to the treatment of AAAs, it should be appreciated that it is applicable to the treatment of any aneurysm, such as those in the descending thoracic aorta, in the peripheral vasculature, and in the brain. Any graft, stent-graft, balloon, or the like insertable into an aneurysm sac or other bodily cavity is suitable for use in the current invention as the insertable medical device, such as the ANEURX AAADVANTAGE®, TALENT®, and ENDURANT® stent-grafts manufactured by Medtronic, Inc. Such stent-grafts typically include a metallic scaffold supporting a synthetic material, such as a woven or unwoven mesh or fabric that is placed over, within or around the scaffold. The stent-graft expands into place after being delivered through an EVAR procedure, as is known in the art. Although the stent-graft shown in FIG. 1 is a so-called "branched" or "bifurcated" stent-graft because it branches into legs 151, 152, it should be recognized that unbranched stent-grafts (i.e., stent-grafts that are not bifurcated into legs) are suitable for use in the present invention. Also suitable for use in the present invention are fenestrated stent-grafts, or chimney or snorkel grafts as are known in the art.

Regardless of whether a branched or unbranched stent-graft is used, the stent-graft will include a first end 160, second end 161 and/or 162, and a lumen 170 extending there between. The first end 160 of stent-graft 150 is secured to a first end 111 of aneurysm 110. As used herein, a graft or stent-graft is said to be "secured" to the end of an aneurysm if it is held into contact with surrounding tissue, such as by friction fit without the use of any securing means or alternatively with the use of such securing means such as barbs, staples, sutures, adhesives, or other suitable securing means. The second end 161 and/or 162 of stent-graft 150 is secured to a second end 112 of aneurysm 110 to span the aneurysm and form a stable channel for blood flow within abdominal aorta 115.

As an alternative to stent-grafts, the present invention may be used with tubular grafts that are unsupported by stent scaffolds. As another alternative, the present invention may be used with one or more inflatable balloons, which are temporarily inserted into the patient as the medical device, around which the in-situ forming foam is delivered.

Figure 2:
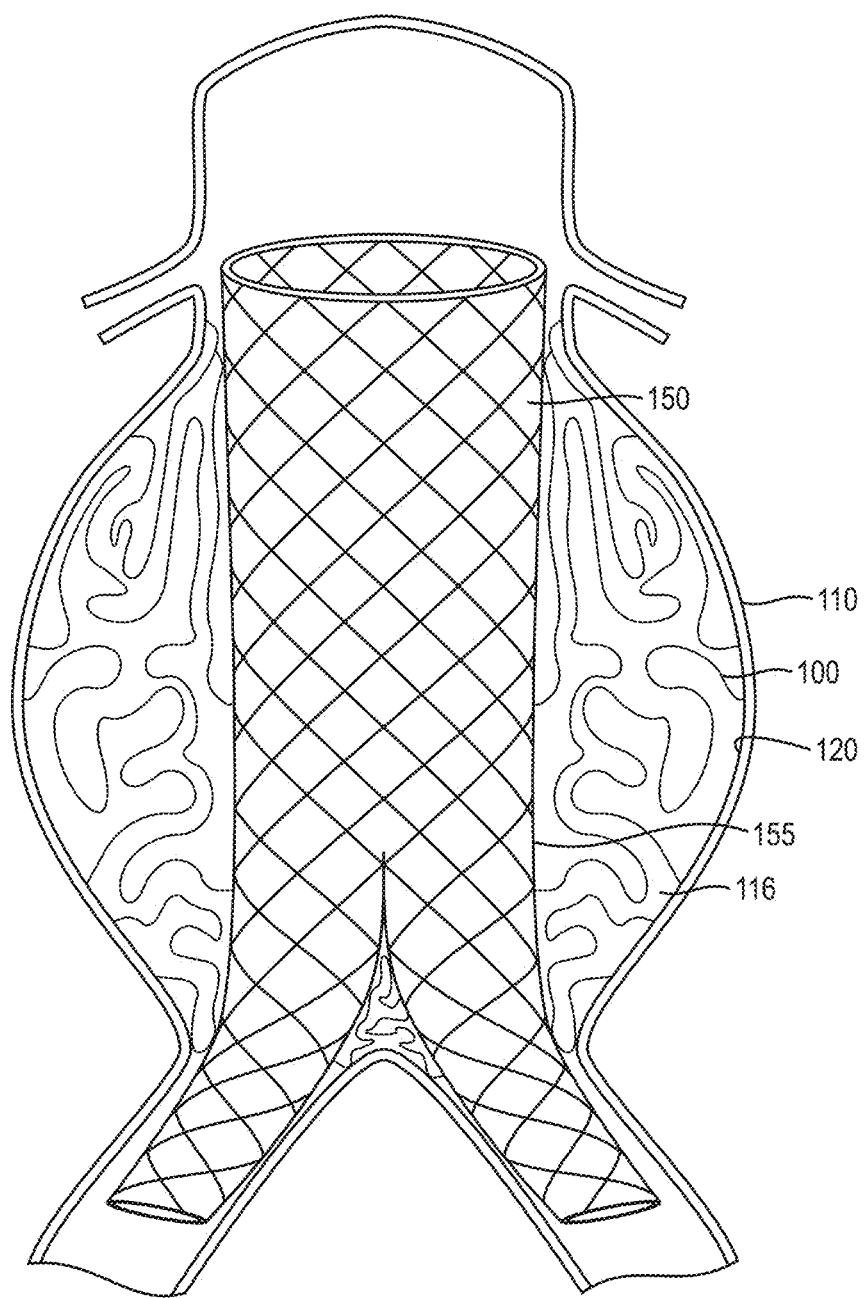
FIG. 2 shows an embodiment of the present invention in which an in-situ forming foam has been placed in the space between a stent-graft and an aneurysm sac.

In accordance with the present invention, after the graft, stent-graft or balloon is placed within an aneurysm, an in-situ forming foam or coil coated with a material which expands to form a foam is inserted between an exterior surface 155 of the medical device (such as stent-graft 150) and a tissue surface 120 of aneurysm 110. In a preferred embodiment as shown in FIG. 2, the in-situ forming foam 100 may substantially fill the aneurysm sac 116. Because of the in-situ forming nature of the foam 100, it preferably expands to contact substantially all tissue surfaces defining the aneurysm sac 116, including penetrating into blood vessels and any other lumens opening into the aneurysm. Depending upon chemistry and delivery system, the foam 100 hardens firstly on the exterior to form a skin, which encases the formulation, promotes material cohesion, and resists material deformation and movement into collateral vessels or outside the targeted area. The interior of the material hardens more slowly via the same or a secondary process. Alternatively, the foam 100 may only partially fill the aneurysm sac 116. In various embodiments, the foam 100 is placed into contact with the exterior surface 155 of stent-graft 150, the tissue surface 120 of aneurysm 110, both of these surfaces, or neither of these surfaces. The exterior surface 155 of the medical devices of the present invention are preferably generally substantially solid, meaning that they include some porosity but are sufficiently solid to prevent substantial quantities of foam from flowing therethrough.

As used herein, a "foam" refers to an article comprising a plurality fluid-filled (i.e., with gas or liquid) of cells (i.e., volumes) that are at least partially surrounded by a material comprising a polymer, and is preferably biocompatible and nonabsorbable. The cells within the foam may be open or closed. The cells within the foam may be any suitable size, such as one or more nanometers, microns, millimeters, or centimeters. The cell size may be substantially uniform throughout the foam, such as where at least 90% of the cells are the same order of magnitude in size, or may have a wide size distribution spanning two or more orders of magnitude. In some embodiments, the polymer foam may comprise at least 10 cells, at least 100 cells, at least 1000 cells, at least 10,000 cells, or more. The foam is formed in-situ substantially commensurately with the delivery of a foam-forming formulation into the aneurysm sac, whereupon it reacts with blood present within the sac, or with saline, water or other suitable fluid delivered together with the polymer, or with another aqueous environment. Such fluid may pre-exist at the delivery site (as in the case of blood) in a so-called "one-part system," or it may be delivered to the site concurrently with the formulation or it may be pre-mixed with the formulation shortly before delivery in so-called "two-part systems." In such two-part systems, the fluid delivered with (or pre-mixed with) the formulation is preferably saline, water or buffered aqueous solution.

The formulation material can comprise a plurality of polymers or prepolymers that can be, for example, cross-linked to each other in the process of forming a polymer foam. In some embodiments, the formulation comprises fluid polymers (including, for example, amorphous polymers with glass transition temperatures below room temperature, or crystalline polymers with melting and glass transition temperatures below room temperature) in the substantial absence of a carrier fluid. In other instances, the plurality of polymers in the formulation are suspended in a carrier fluid (e.g., a liquid suspension medium, emulsion, dispersion, etc.) or dissolved in a carrier fluid to create a homogeneous phase. The term "polymer" is given its ordinary meaning in the art, and is used to refer to a molecule that includes a plurality of monomers. Included within the definition of "polymer" are "pre-polymers," which are a subclass of polymers that are characterized by reactive groups in the polymer chain. Such pre-polymers are of particular use in the present invention because the reactive groups in such polymers help drive the in-situ forming foam reaction. In some embodiments, a polymer may comprise fewer than about 100, fewer than about 50, fewer than about 25, or fewer than about 10 monomer units. In some embodiments, a polymer may comprise between about 2 and about 100, between about 2 and about 50, between about 2 and about 25, between about 5 and about 50, or between about 5 and about 25 monomer units. The polymers within the formulation can comprise a variety of functional groups that allow the polymers to, for example, cross-link to each other, attach to tissue or other material within the aneurysm sac, interact with agents in the bloodstream of the subject (e.g., imaging agents, cross-linking agents, etc.), among other functionalities.

In some embodiments, the polymers within the formulation may cross-link within the aneurysm sac. The term "cross-linking" is used to refer to the process whereby a pendant group on a first polymer chain may react with a second polymer chain (e.g., a pendant group on the second polymer) or other molecule or molecules to form a covalent or ionic bond joining the two polymers. Polymers that can undergo cross-linking can comprise straight chains, branched chains having one or more arms (i.e., multi-arm chains), or mixtures of these. In some cases, the polymer (branched and/or non-branched) may contain reactive side chains and/or reactive terminal groups (i.e., groups at the end of a polymer chain), and cross-linking may involve reactions between the side chains, between terminal groups, and/or between a side chain and a terminal group. In some instances, the formulation may be substantially free of polymers that comprise reactive groups on terminal monomers. In other cases, the formulation may comprise a substantial amount of polymers with reactive groups on terminal monomers. In some embodiments (e.g., in some cases in which branched polymers are employed) a relatively large percentage of the cross-linking reactions (e.g., at least about 70%, at least about 80%, at least about 90%, at least about 95%, at least about 99%, or substantially all of the cross-linking reactions) can occur between terminal reactive groups.

Cross-linking may commence via a variety of mechanisms. In some embodiments, polymer may cross-link once the polymer contacts moisture (e.g., water, blood, aqueous solutions, etc.), for example, within an aneurysm sac. Cross-linking may be achieved via acrylate, methacrylate, vinyl, cinnamic acid, or acrylamide groups in some embodiments. Such groups may be cross-linked via the application of ultraviolet radiation and can be used in conjunction with an external foaming agent. In some instances, a cross-linking initiator may be introduced into the subject in which the aneurysm sac is located (e.g., via the bloodstream, via a separate container in the delivery system such that the initiator and the polymer do not mix before delivery, etc.) to initiate cross-linking of the polymer. For example, a free radical initiator, such as eosin or 2,2-dimethoxy-2-phenylacetophenone, can be used to initiate cross-linking of polymers bearing acrylate, methacrylate, or vinyl groups. Other examples of reactive groups on polymer chains that can be paired to produce cross-linking include, but are not limited to, hydroxyls and isocyanates, amines and NHS-esters, thiols and maleimides, azides and alkynes (i.e. "click chemistry"), acid chlorides and alcohols, and in a preferred embodiment, isocyanates and polyols. It may be desirable, in some embodiments, to keep these paired chemicals separate until they are introduced into the aneurysm sac to prevent unwanted cross-linking outside the aneurysm sac. For example, the polymer may include azide functional groups, and alkynes can be introduced to the aneurysm sac from a container separate from the container used to introduce the polymer. In some embodiments, these chemistries are also employed in conjunction with an external foaming agent. As the formulation cross-links, its viscosity may be increased. In some cases, the cross-linking proceeds until a cellular solid material (e.g., a solid elastomeric foam) is formed.

In some embodiments, a gas is formed from the reaction of the polymer supplied to the aneurysm sac. For example, in some embodiments, the foaming step comprises reacting one or more pendant groups on the polymer or cross-linked product to form a gaseous product. The gas-producing pendant groups may react upon contact with another material in the aneurysm sac. For example, in some cases, the gas producing groups may react upon contact with moisture in the aneurysm sac. In some cases, the gas-producing pendant groups may react with a chemical supplied to the aneurysm sac separately from the formulation (e.g., via the bloodstream, via an external source separate from the polymer material source, etc.). In some embodiments, the gas-producing pendant groups on the polymer chain may react with another component that is supplied to the aneurysm sac. In some embodiments, the polymer or cross-linked product may comprise $CO_2$-producing groups. $CO_2$ producing groups are preferred due to the biocompatibility of $CO_2$ and high solubility of $CO_2$ in blood. Examples of $CO_2$-producing groups include, but are not limited to, isocyanate groups, carbonates, bicarbonates, and carbamates. Such groups may produce $CO_2$ gas when reacted with an acid, for example. In some cases, the $CO_2$-producing group may include an N-hydroxysuccinimide carbonate, illustrated below:

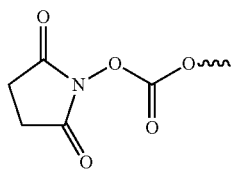

$CO_2$-producing groups may include, in some cases, imidazole carbamates, as illustrated below:

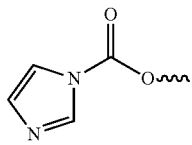

As noted above, in some embodiments, the foaming and cross-linking steps occur substantially simultaneously. In some cases, the foaming and cross-linking steps may occur substantially simultaneously, but remain independent of each other. For example, the formulation may cross-link by reacting with water in the aneurysm sac, and, at substantially the same time, gas may be introduced to the formulation from an external container. In another embodiment, a first material containing gas generating groups may produce gas by contact with a second agent (e.g., water in the body, water supplied separately, or chemical additive), while contact or interaction with a third material leads to crosslinking. For example, at the time of delivery, polymer A with isocyanate groups can be mixed with water and polymer B, in which the former causes the generation carbon dioxide to foam the material and polymer B can contain hydroxyl groups that react with isocyanates on polymer A to form a crosslinked network between polymers A and B.

The foaming and cross-linking steps may be, in some cases, part of the same reaction process. In embodiments of a one-part system, isocyanate hydrolyzes when it contacts water, forming $CO_2$ and an amine. This newly formed amine can react with any remaining unhydrolyzed isocyanate groups, thereby crosslinking the material. In this case, gas evolution and crosslinking occur together, where the latter is dependent upon the former for it to occur. In other examples, one or more reactions may produce a gaseous by-product which serves as the supply of gas to form the polymer foam, but concurrently leads to the generation of new functional groups that enable crosslinking. The gaseous by-product can be trapped within the formulation and coalesce to form bubbles. As the reaction progresses, the formation, growth and expansion of the gas bubbles can expand the polymer volume and force it into interstitial areas of the aneurysm sac. As the polymer cross-links, a three-dimensional foam can be formed within the aneurysm sac. The volume expansion and cross-linking can serve to coat and form a seal with surfaces of the aneurysm sac, and optionally provide internal compression, which may be useful, for example, in controlling movement of blood and stabilizing the stent graft. In addition, such a reaction scheme can be combined with an external supply of gas (e.g., $CO_2$ in an external container) to increase the amount of gas contained in the formulation or a cross-linked product of the polymer.

All of the foaming mechanisms described herein may occur before any substantial cross-linking has occurred or during cross-linking of the formulation or a cross-linked product of the formulation. For example, in some cases, an external gas may be introduced into and dispersed within a formulation that has not substantially cross-linked. The formulation may then cross-link around the bubbles to form the foam. In such cases, the viscosity and surface tension of the formulation can be chosen such that the material is able to retain bubbles within the volume without the need for cross-linking. In another embodiment, a surfactant can be added to the formulation to create a formulation that retains gas bubbles without the need for crosslinking. In some embodiments, at least some cross-linking may occur before the gas is introduced to the formulation, and the gas is dispersed within a partially cross-linked formulation that has not completely solidified to form a foam.

In a preferred embodiment, the foam is formed by a fast cross-linking reaction that can be surface triggered by in-situ water. Multi-functional moisture sensitive silanes are one example of materials susceptible to such reactions especially when formulated with tin, titans or other metal-organic catalysts. One-part cross-linking systems can be created by a two-step process. In the first step, hydroxyl containing siloxanes (either silanols or carbinols) are reacted with an excess of multifunctional silane containing acetoxy, oxime, alkoxy (e.g., methoxy, ethoxy), isopropenoxy, amide, amine, aminoxy, or other functional groups containing silane with the hydrolytically susceptible Si—O—C bond. The resulting prepolymers have multiple groups that are susceptible to hydrolysis. In the second step, such prepolymers are exposed to in-situ water to result in a rapidly cross-linking elastic solid. The reaction proceeds from the outside-in, resulting in a quickly formed outer skin and, in some cases, the formation of the foam into a coil-like configuration. The slower permeation of water or alternative reaction trigger can be used to slowly cure the material inside of the skin. The proteins and pH of the blood can be used to support coil formation by modifying the rate of the skin-forming reaction as well as in coating the formed coil and preventing coil sticking and agglomeration upon self-contact.

Additionally, hydride functional (Si—H) siloxanes or isocyanate functionalized carbinols can be introduced into silanol elastomer formulations to generate gas and produce expanding foamed structures. Expansion of the material can be used to increase the size of the formed coil effectively decreasing coil embolization potential. Expansion of the material can also be critical to increase material size without delivery of more material, in adding porosity and in generating sealing or pressure. Additional formulation ingredients such as surfactants can be used to the impact of generated gas on porosity and expansion.

In an alternative embodiment of this invention, acetic acid and sodium bicarbonate are mixed and caused to reach together in-situ to produce carbon dioxide as a blowing agent. An additional by-product of the reaction is water, which can accelerate an independent isocyanate gelling reaction.

Alternatively, isocyanate-containing prepolymers are a second example of materials that may be used to generate in-situ forming coils or lava-like foams. Isocyanate groups are relatively unstable when exposed to water and moisture. One-part isocyanate based cross-linking systems can be created by a two-step process. In the first step, polyols, diols, diamines, polyamines, diepoxides or polyepoxides are capped with aliphatic or aromatic diisocyanates such as isophorone diisocyanate (IPDI), dexamethylene diisocyanate (HDI) and methylene diphenyl diisocyanate (MDI). Additionally, multifunctional isocyanates such as HDI biuret, HDI trimer, and polymeric MDI can be combined with diols or diamines. The resulting prepolymers have multiple distant isocyanate groups that are able to react with water and amines found in blood. In the second step, such prepolymers are exposed to in-situ blood resulting in rapid cross-linking and foam formation. The reaction is water-triggered and proceeds from the outside-in, forming a porous outer skin, lava-like shell core structure that assists in coil formation. The expansion of such materials can be important in generating coils of a large diameter while maintaining a small cross-sectional area of the delivery device. Such materials can be used to form stand-alone foaming or gelling coils or combined with each other such that one material is coaxially formed on top of the other. For example, a coaxial delivery device can deploy a coil forming formation surrounded by a highly expandable coating formulation. The two formulations may be from different chemistry classes. Alternatively, the two formulations may be selected to be immiscible such that upon mixing together that the formulations phase separate (e.g., oil miscible and water miscible formulations) to naturally form a coaxial structure. Additionally, the interaction with the catheter wall and/or the density differential of the two fluids can be used to further drive the phase separation. Additionally, two-part formulations may be designed such that the two parts are not fully miscible. A surfactant system may be used to formulate the two part formulation into a single stable emulsion. Such an emulsion could be delivered via single chamber delivery device and does not require mixing. The emulsion can be destabilized by shear during delivery or in-situ factors (pH, temperature, ionic strength). Upon such destabilization, the internal phase of the emulsion would spill out and trigger the reaction with the external phase resulting in in-situ foam formation.

The solidification of interior portions of foams that form with an exterior skin can be controlled, for example, by altering the permeability of the material to a solidification trigger. In the case that the trigger is water, permeability can be controlled by adjusting material hydrophobicity. Additional ingredients can be added to adjust material radiopacity, density, and/or contact angle with blood, tissue, or other biological matrices.

The properties of the polymer used to form the polymer foam may be tailored to achieve a desired result. For example, in some embodiments, the viscosity of the polymer is tailored such that the polymer formulation is better able to permeate the aneurysm sac and create conformal contact with the sac wall and/or the medical device placed within the aneurysm. An overly viscous polymer formulation may require excessive pressure to deploy within the aneurysm sac. In addition, an overly viscous polymer formulation may inhibit the polymer from accessing interstitial spaces. An overly low-viscosity polymer formulation might be difficult to contain the material to the injured site or may be displaced by the flow of a bodily fluid. One of ordinary skill in the art will be able to produce the desired viscosity for a given polymer type by, for example, adjusting the molecular weight of the polymer. In some embodiments, the viscosity and the molecular weight are related through a power law. The molecular weight of a polymer may be adjusted by, for example, controlling the time of the polymerization reaction used to generate the polymer. In some embodiments, the molecular weight of the polymer is between about 1000 and about 10,000 g/mol or between about 1200 and 6000 g/mol. The viscosity of the formulation may be adjusted by, for example, adding diluents such as any suitable low molecular weight, low viscosity compound, examples of which include triacetin, propylene carbonate, tetraethylene glycol dimethyl ether, dimethyl esters of diacids (e.g., diethyl malonate, dimethyl adipate), dimethyl sulfoxide, and oils (vegetable, olive, castor, etc.). In some embodiments, the polymer is amorphous or semi-crystalline with a glass transition temperature (TO below room temperature. Such properties yield, in some cases, polymers with sufficiently low viscosities that they can be dispensed from an external container via pressure-driven flow.

In some embodiments, properties or composition of the polymer may be chosen to achieve a desired hydrophilicity or hydrophobicity. The hydrophilicity of the polymer may be selected, in some instances, such that the surfaces (e.g., tissue surfaces) within an aneurysm sac are appropriately wetted. Generally, a material with increased hydrophilicity will have a greater tendency to wet soft tissues surfaces and to react more quickly because of better mixing with blood. However, the polymer and resulting polymer foam may be, in some cases, somewhat hydrophobic such that they do not dissolve into biological fluids. Appropriately hydrophilic polymers are capable of conformally wetting interior surfaces of an aneurysm sac while remaining contained within the cavity. In some embodiments, the composition of the polymer may be selected to achieve a desired hydrophilicity. For example, in some embodiments, the chain length of a monomer used to synthesize the polymer can be varied to change hydrophilicity. As a specific example, the carbon chain length between carbonyl groups of a diacid monomer can be varied from between two and eight aliphatic carbons, producing a range of hydrophilicity in the resulting polymer. A more common example for modulating hydrophilicity may be to generate a co-polymer composed of some hydrophilic and some hydrophobic monomers.

In some embodiments, the polymer foams described herein may have favorable mechanical properties. In some embodiments, the polymer foams are elastomeric. The term "elastomer" as used herein, refers to a polymer that can return to the approximate shape from which it has been substantially distorted by an applied stress. In some cases, the elastomeric polymer foams described herein may comprise a polymer having a bulk modulus of between about 0.05 MPa and about 10 MPa; 0.05 MPa and about 100 MPa; and 0.05 MPa and about 500 MPa. Elastomeric polymers may be particularly suitable for use in making polymer foams because they are capable sustaining stress without permanently deforming, while providing adequate support for body organs and tissues.

Additionally, the density of the formulation or polymer foam may be purposely manipulated. In some embodiments, the formulation and/or polymer foam will have a density less than that of blood, such that it will rise to the top of the sac during filling. Alternatively, the formulation and/or polymer foam might have a density greater than that of blood such that it will fall to the bottom of the sac. The density of the formulation may be manipulated by incorporating gas or addition of fillers or additives (e.g., tantalum) or other techniques known to those in the art.

The time required to form the polymer foam after exposure of the formulation to the aneurysm sac and the final mechanical and physicochemical properties of the polymer foam can depend on such factors as the composition of the polymer and its hydrophobicity, the density of pendant groups (e.g., cross-linking groups), relative positions of the pendant groups (e.g., cross-linking groups), and other factors.

In some embodiments, the polymer or polymer foam may be biodegradable. As used herein, "biodegradable" describes materials that are capable of degrading down to oligomeric or monomeric species under physiological or endosomal conditions. The phrase "physiological conditions," as used herein, relates to the range of chemical (e.g., pH, ionic strength) and biochemical (e.g., enzyme concentrations) conditions likely to be encountered in the intracellular and extracellular fluids of tissues. In some embodiments, the physiological pH ranges from about 7.0 to 7.4. In some embodiments, biodegradable materials are not hydrolytically degradable but can be fully degraded via enzymatic action to fully degrade. In some cases, biodegradable materials are hydrolytically or enzymatically degradable, or combinations thereof. In some embodiments, the polymer or polymer foam is biodegradable, but it does not biodegrade over the time scale in which it is located within an aneurysm sac. In such cases, the polymer foam can remain structurally stable while being inserted into the aneurysm sac, while ensuring that any remnants of the polymer foam that remain within the aneurysm sac after removal can be biodegraded.

The polymeric foams described herein may be used, in some embodiments, to prevent or limit the movement of a bodily fluid within the aneurysm sac or other bodily cavity, relative to an amount of movement of bodily fluid that would occur under essentially identical conditions in the absence of the polymer foam. "Essentially identical conditions," in this context, means conditions that are similar or identical other than the presence of the polymer foam. For example, otherwise identical conditions may mean that the aneurysm sac or other bodily cavity is similar or identical, the conditions within the cavity are similar or identical, but where no polymer foam is located within the aneurysm sac or bodily cavity. In some embodiments, the polymer foam may be used to reduce the movement of blood or other bodily fluid within an aneurysm sac or bodily cavity.

The movement of bodily fluids may be prevented or limited over a relatively long period of time. In the primary embodiment, the foam forms a permanent hemostatic implant within the aneurysm sac or bodily cavity.

In some cases, the movement of bodily fluids may be prevented or limited via the application of pressure. For example, the formation of the polymer foam may involve volumetric expansion of the polymer. In some embodiments, the expansion of the polymer may result in the application of a pressure to a surface within the aneurysm sac or bodily cavity, potentially forming and improving the seal.

In some cases, the movement of bodily fluids may be prevented or limited due to a physical seal created between the aneurysm wall or collateral vessel walls (e.g. inferior mesenteric artery, lumbar arteries) and the surface of the foam. This seal may be due to pressure and/or chemical bonding between the tissue surface and foam and/or the highly conformal contact of the foam with the tissue surfaces combined with the foam's tendency to induce coagulation of blood. In addition, the foam may penetrate collateral vessels within the aneurysm sac to further limit blood flow into the sac. Preferably in-situ expansion of the foam in combination with formation of the skin or coil leads to penetration of these collateral vessels by less than about 2 cm. In some cases, the polymer may be designed to cross-link quickly, for example, by tailoring the polymer to have functional groups that crosslink quickly, by adding catalysts, or by other known means. Suitable catalysts for use in embodiments of the present invention include amine based compounds, preferably tertiary amines, triethylenediamine (TEDA, DABCO, DABCO 33-LV), bis(2-dimethylaminoethyl)ether (Niax A1), trimethylaminoethyl-ethanolamine, 1,2-dimethylimidazole. In addition, the pores of the foam can trap blood and allow it to coagulate in stagnant areas. In some cases, the movement of the stent or another medical implant (stent migration) may be minimized due to the encapsulation of such a device by the foam. The foam may be used to surround and reinforce the device, increasing mechanical robustness (allowing for thinner, intrinsically weaker stent design).

In addition to gas-forming pendant groups, other active agents may also be included as pendant groups on the polymer. For example, the polymer foam can include groups used to stimulate desirable cellular responses such as fibroplasia, angiogenesis and epithelialization. Similarly, the mechanical structure and mechanical properties of the foam itself may elicit these properties. In some embodiments, the polymer or polymer foam may be covalently bonded to a surface within the aneurysm sac, for example, through a pendant group.

In some embodiments, the polymer or cross-linked product may comprise at least one pendant group that can bind to tissue or injured tissue (e.g., inflamed tissue, bleeding tissue, a wound site, etc.) within the aneurysm sac. The binding of the pendant groups to the tissue or injured tissue can be covalent or non-covalent. The tissue or injured tissue may comprise one or more molecules that would not be present in or near uninjured tissue as is the case, for example, when subendothelial surfaces are exposed. By including such pendant groups, a polymer or cross-linked product could be made that selectively binds to tissue or injured tissue, in comparison to uninjured tissue. Such binding may limit or prevent the movement of bodily fluid within the aneurysm sac, in some embodiments. Examples of chemicals that may be targeted by pendant groups on the polymer or polymer foam include, for example, von Willebrand Factor, collagen (e.g., collagen I and IV), a fibroblast growth factor, laminin, elastin, localized coagulation factors in their activated form (e.g., fibrin, thrombin, factor Xa, etc.), among others. Example of types of pendant groups that may be bound to the polymer or polymer foam for such uses include, for example, peptides, carbohydrates (e.g., oligosaccharide sequences), aptamers.

In addition to targeting tissues or injured tissues, pendant groups may be used to stabilize tissue or injured tissue. For example, pendant groups (e.g., $CO_2$-forming groups) may covalently bond to tissue, in some cases, which may lead to the sealing of one or more openings within an aneurysm sac. Such binding can aid in limiting or preventing the movement of bodily fluid within the aneurysm sac, in some cases. In some embodiments, the concentration of isocyanate in the polymer or a cross-linked product can affect the extent to which binding between the polymer and tissue occurs. Specifically, increasing the isocyanate levels can serve to increase and reinforce the polymer-tissue contact area, potentially producing a stronger and longer-lasting seal. Increasing the level of isocyanate in the polymer can also increase the crosslink density, potentially resulting in a more rigid material that may break more easily at the polymer-tissue interface (e.g., when the body is moved). Therefore, the concentration of isocyanate may be selected, in some cases, to balance between these two effects.

In another embodiment, the polymer properties are selected such that minimal covalent binding of the foam to tissue is observed. The foam, however, can be bound to tissue by different non-covalent forces, such as electrostatic, Van der Waals, or capillary. Minimal covalent binding of foam to tissue can facilitate easy foam removal and prevent adhesions, such as abdominal adhesions, during the healing process.

In some cases, non-isocyanate pendant groups may be used to stabilize the polymer-tissue interface. For example, the polymer may comprise aldehyde reactive groups, which can be used, for example to bind tissue proteins. Aldehyde groups may be attached by, for example, attaching ethanolamine to the polymer, followed by oxidizing the pendant hydroxyl group to form an aldehyde group. In some instances, pendant groups that selectively bind to fibrin may be used to stabilize the clot-polymer interface. In addition, pendant groups may be selected that compete with plasminogen and its activators for fibrin binding sites, blocking the activation of fibrynolytic cascade.

In some instances, a drug may be delivered to the aneurysm sac with the formulation. In some embodiments, the formulation may comprise a drug. For example, a drug (or a plurality of particles containing one or more drugs) may be dispersed within the formulation. Example of such drugs include, but are not limited to, antifibrinolytic compounds (e.g., aminocaproic acid, tranexamic acid, etc.), anti-fibrotic compounds, antimicrobial compounds (e.g., antibiotics), anti-inflammatory compounds, analgesics, pro-coagulant compounds, statins, growth factors, and vasoconstrictors. Drugs that comprise amine groups may, in some cases, be isolated from isocyanates within the formulation, for example, to prevent unwanted reaction during the cross-linking step. Isolation can be achieved by encapsulating drugs into secondary particles and loading them into the formulation at the time of delivery to the aneurysm sac. In addition, encapsulation may be used to release the drugs at a controlled rate. In some embodiments, a drug may be incorporated into a fiber, which may be included in the formulation. The drug release rate from the fiber can be controlled by varying composition and structure (e.g., thickness or other dimension, presence of sheath) of fiber. For example, the fiber can be designed to deliver an initial burst release shortly after the deployment of the formulation, followed by sustained delivery (e.g., over the time period in which the formulation foam will be left in the aneurysm sac).

The formulation may be combined with a second agent (and, optionally, a third agent, fourth agent, etc.), in some cases, before or after the formulation is transported to the aneurysm sac. The second agent may comprise, for example, a compound that accelerates at least one of cross-linking and foaming, relative to a rate of at least one of cross-linking and foaming that would have occurred in the absence of the second agent. For example, in some embodiments, the second agent may comprise an amine (e.g., a polyamine). The amine compound may serve to increase the rate at which the formulation cross-links, which may also reduce the amount of time required to reduce or eliminate the movement of a fluid (e.g., blood) within the aneurysm sac. The second agent may comprise, in some cases, at least one of lysine, spermine, spermidine, hexamethylenediamine, polylysine, polyallylamine, polyethylenimine, and chitosan. In some cases, the second reagent may comprise a carbonate or a bicarbonate which may be used, for example, to produce $CO_2$ gas in-situ, as described above. In some embodiments, the second reagent can comprise an acid which may be used, for example, as a reactant in the $CO_2$-producing reaction. The acid functionality may comprise, for example, a carboxylic acid pendant group attached to a polymer chain or blended with a polymer to form a mixture. In some cases, the second reagent can be native in the body (e.g., bicarbonate in the blood). In other cases, the second agent may originate from outside the aneurysm sac. For example, the second agent may be, for example, supplied to the aneurysm sac along with the formulation.

In some embodiments, the combination of the second agent with the formulation produces a polymer foam with significantly different mechanical properties (e.g., elastic modulus, yield strength, breaking strength, etc.) than would have been produced in the absence of the second agent. For example, addition of the second agent may lead to increased cross-linking among polymer molecules, potentially producing a stiffer foam. In another embodiment, the second agent may have a high molecular weight, such that the distance between crosslinks is high, and the resulting foam is softer.

In other embodiments, particles or fibers are included in the foam formulation to result in a composite structure which provides desirable mechanical properties. For example, biocompatible polymer fibers may be included in the unreacted components. These fibers will distribute throughout the foam during in-situ expansion and become part of the structure upon crosslinking. These fibers can provide a more durable, stronger or higher modulus implant. Addition of space filling, highly-compliant particles or fibers may alternately provide a lower modulus, but also more durable implant. Inclusion of fibers which constrain the expansion of the foam may also prevent or limit foam expansion into collateral vessels in the aneurysm sac.

The combination of the second agent with the formulation may, in some embodiments, prevent or limit the flow of blood into the aneurysm sac, relative to an amount of blood flow that would occur under essentially identical conditions in the absence of the second agent. In some embodiments, blood flow may be reduced due to the increased rate of cross-linking or foaming mentioned above. In some cases, the second agent may comprise a pro-coagulant compound (e.g., thrombin, fibrinogen, factor X, factor VII, kaolin, glass, chitosan, or other hemostatic agent).

The second agent may be stored in a container separate from the formulation, for example, to prevent unwanted reaction between the formulation and the second agent outside the aneurysm sac. In some embodiments, a container can be used that keeps the formulation and the second agent separated while stored or transported, but allow for mixing at the outlet nozzle or within the aneurysm sac when the contents are expelled. The outlet nozzle can mix multiple components (>2) including gases in a static or dynamic manner. Examples of static mixers are helical mixers, Low Pressure Drop (LPD) mixers, square element mixer (Quadro), GXF and Interfacial Surface Generator (ISG) mixers. Examples of dynamic mixers are impellers, and rotary static mixers. Nozzles will handle low and high pressure differentials during dispensing. The container may also be designed to mix the components immediately prior to dispensing by breaking the barrier between each of the components and allowing them to mix. Mixing can occur manually such as shaking the canister or chambers can be under vacuum and when the barrier is broken a vortex will be created to mix the components.

In another embodiment, additives can be added to the formulation that absorb heat if generated during the cross-linking reaction. For example, materials in the form of micro or nano-particles, spheres or fibers can absorb the heat by undergoing a phase change (e.g. melting) or glass transition and thereby reduce the heat absorbed by biological tissues. For example, biodegradable fibers made of polycaprolactone can melt at ~60° C., absorbing the generated heat and reducing tissue damage.

In some embodiments, the aneurysm sac can be imaged. The ability to image the aneurysm sac can allow for proper dosing, efficient localization and repair of an injury, stabilization of a wound, etc. In some embodiments, contrast agents can be incorporated into the formulation. In other embodiments, pendant groups on the polymer or polymer foam can be utilized to aid in imaging the aneurysm sac. For example, a contrast agent can be introduced into the blood stream of a subject in which the aneurysm sac is located, and the contrast agent may be capable of selectively binding to pendant groups of the polymer. Examples of contrast agents include, for example, colored, fluorescent, or radio-opaque imaging entities. Examples of radio-opaque imaging entities include, for example, barium-based substances, iodine-based substances, tantalum powder, tantalum oxide powder, tantalum-based substances, and zirconium dioxide. In another embodiment the foam itself provides sufficient radio contrast to surrounding tissues to facilitate visualization. For example, gas bubbles or gas-filled pores may provide contrast upon imaging with ultrasound. In some embodiments, the contrast agents emit electromagnetic radiation in the near-infrared range (e.g., about 700 to about 1000 nm) upon interacting with the polymer foam. As a specific example, quantum dots (QD) may be used as contrast agents. In some cases, fluorescent organic tags (e.g. fluoroscein isocyanate) or radio-opaque chelating groups (e.g., Gd3+) can be used with appropriate imaging equipment. In another example, the contrast agents listed above may be attached as pendant groups to the polymer or dispersed in the polymer to aid in visualization. In another example, tantalum, titanium or barium sulfate powder may be physically mixed with the polymer for visualization. To provide a time-dependent contrast, the foam may include bio-erodible particles or fibers which include the contrast agent. Following exposure to a physiological environment, the particles or fibers will erode and release the contrast agent which can then be eliminated from the implant site. This can provide implants which become less radio-opaque, for example, over time post delivery. This may be advantageous to users who want to evaluate location of the foam for some time after implantation, but then do not desire to have a radio-opaque foam providing imaging artifacts which limit assessment of surrounding tissues. Preferably the radio-opacity will decrease substantially within three months of implantation.

A variety of mechanisms can be employed to remove polymer or polymer foam from the aneurysm sac or from placement on tissue, if desired. In some embodiments, at least part of the polymer foam is removed via surgical intervention. For example, the polymer foam may be cut out of the aneurysm sac, in some instances. In some cases, surgical intervention may be sufficient to remove the bulk of the polymer foam material (e.g., at least about 80%, at least about 90%, etc.) from the aneurysm sac. The polymer or the pendant groups bonded to the polymer may be selected, in some cases, such that the resulting polymer foam can be removed from an aneurysm sac. In some embodiments that employ a biodegradable polymer or polymer foam, the foam or the remainder of the foam after surgical removal may biodegrade over time. In other embodiments, the foam is permanently implanted in the patient.

In another embodiment drug-loaded objects are incorporated in the formulation at or before administration. Incorporation of drug-loaded objects into a formulation during administration is accomplished by those methods known to those skilled in the medical and pharmaceutical formulation arts. Examples of drug-loaded objects include: microspheres, microfibers, core-sheath microfibers, core-sheath nanofibers, nanoparticles, nanospheres, nanofibers or pure particles of drug. Preferably drug is released from these objects over a period of 7 days. More preferably the drug is released up to 14 days. Drug may be released for up to 30 days or longer. Preferably the kinetic release profile for the drug provides approximately the same dose of drug throughout a given period of time.

Delivery Systems

Figure 3:
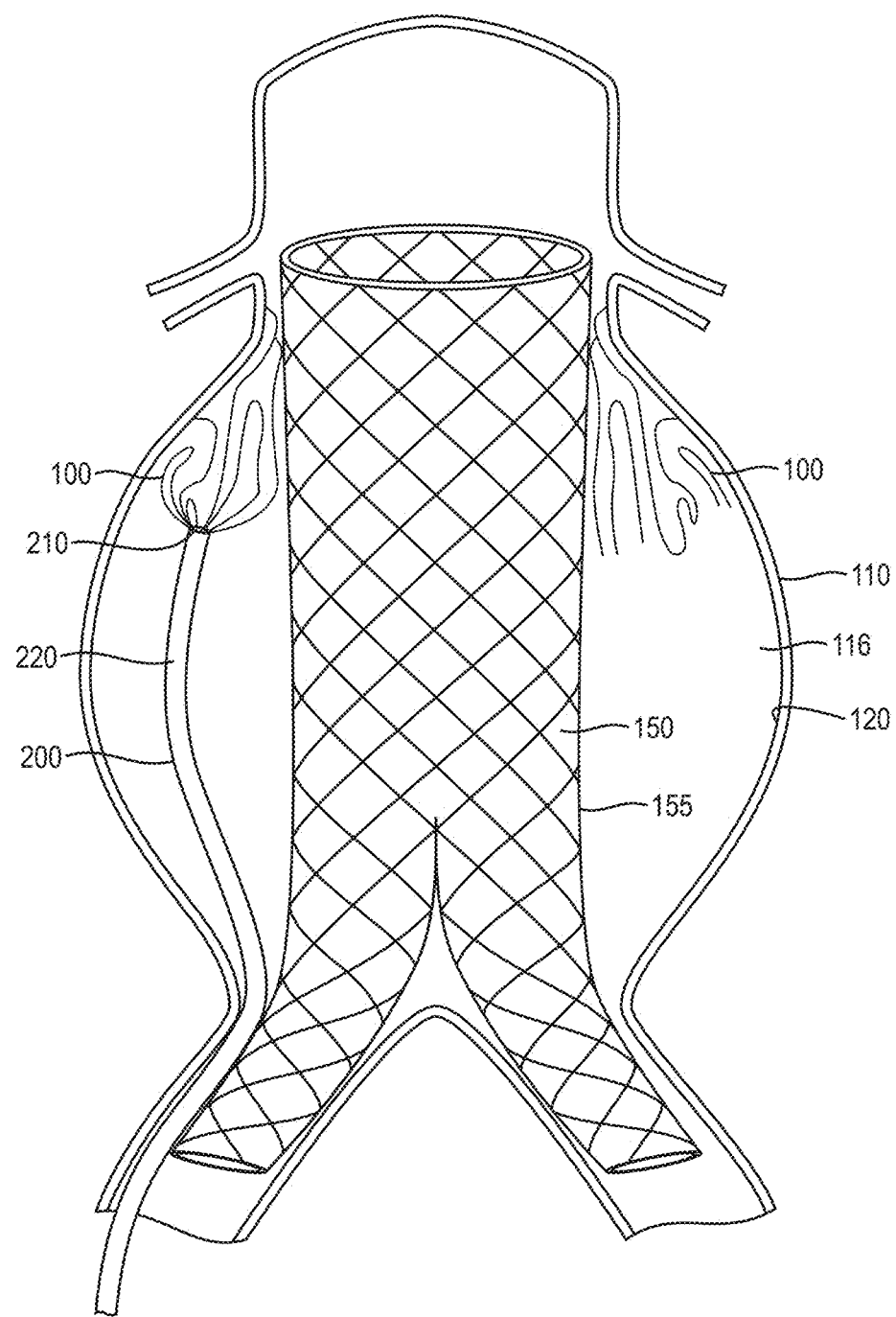
FIG. 3 shows an embodiment of the present invention in which a polymer is delivered into an aneurysm sac and reacts to form an in-situ forming foam.

The in-situ forming foams of the present invention are delivered to an aneurysm site using any suitable delivery means. In one embodiment, the formulation that forms the foam is delivered through a delivery catheter 200, as shown in FIG. 3. The catheter 200 is generally an elongated tube having an open distal end 210 and a lumen 220 extending along the length of the tube. When placed within the aneurysm sac 116, the formulation is extruded from the distal end 210, whereupon it reacts in the presence of blood or other fluid to generate a gas and form a foam 100 in-situ with a robust skin. In some cases where the skin forms rapidly and is likely sufficiently robust mechanically, resulting in a continuous, packable polymer, which tends to form in a coil. Through continued extrusion of the material out of the catheter, the user creates a long coil which fills the aneurysm space. The space may be filled with an aneurysm coil or other medical device and an in-situ forming foam or an aneurysm coil or other medical device that is coated with a material which expands to form a foam coating in-situ. The continuous, long aspect ratio of the coil and cured outer surface prevent the coil from entering the collateral vessels to a significant degree, thus avoiding possible related adverse events.

In another embodiment, the tip of the delivery catheter 200 is designed to prevent clogging by foam components. For example, in one embodiment, the catheter includes an inner hollow tube 220 that includes perforations, holes or the like 230 (as shown in FIG. 4*a*) and/or a mesh or other openings 240 (as shown in FIG. 4*b*) near the distal end thereof. Such features allow for the passage of gas and fluids from the delivery site during delivery of polymer through the distal end 210 of catheter 200. Such gas and fluids, which would otherwise increase the risk of clogging the catheter 200, may passively move out of the delivery space (e.g., an aneurysm sac) by a pressure gradient between the delivery space and ambient atmosphere, or a negative pressure may be applied to the proximal end of the inner hollow tube 220 to actively facilitate removal of gas from the delivery site. In an alternate embodiment, a second catheter may be used to actively or passively remove gas, water, and blood from the aneurysm sac.

In an alternate embodiment, the catheter 200 includes a one-way valve near the distal end 201 to prevent blood from wicking into the catheter and causing premature reaction of polymer therein. In some embodiments, the catheter 200 includes a pressure sensor on or near distal end 210 to indicate completion of foam delivery. Alternately, a pressure sensor is incorporated on or near the proximal end to measure pressure in the delivery lumen. This pressure should accurately reflect the pressure in the aneurysm sac when the user is not infusing material through the lumen and prior to completion of the crosslinking reaction.

Transport to an aneurysm site may be improved by providing formulations that can disperse within the sac before foaming and/or cross-linking Formulations have been generated that have a variety of reaction kinetics, as measured by cream time, gel time, and rise time. Cream time is defined as the time between the start of material mixing and the point at which fine bubbles begin to appear and the foam begins to rise. Gel time is defined as the time at which long "strings" of tacky material can be pulled away from the surface of the foam when the surface is contacted with the edge of a tongue depressor or similar instrument. Rise time is the time at which the foam stops expanding as observed visually. Overall reaction time can be adjusted by factors such as the hydrophilicity of the polymer formulation and amount of catalyst, and in certain embodiments is as short as 1 to 3 minutes, and in other embodiments, is as long as 10 minutes or longer.

Foaming kinetics can be altered by adjusting the types and levels of catalysts and inhibitors used in the formulation. In general, the addition of weak acids such as acetic acid or citric acid may delay the start of foaming. The rate of foaming can be controlled by adjusting the relative levels of blowing and gelling catalysts.

By varying the catheter used to deliver the formulations prone to coil formation, the coil diameter, cross-sectional profile, surface properties and curvature may be controlled. Control of these properties may be critical in achieving the clinical objectives described above. Diameter may be varied by any of the following methods: (i) by modifying the expansion properties of coil forming material, (ii) by modifying the swelling properties of coil forming material, (iii) by varying the diameter of the catheter or size of the opening at or near the top of the catheter and (iv) by coil constriction due to cross-linking.

The shape of a coil's cross section may be varied by fashioning a die in or on the distal tip of the catheter. For example, the die may be designed to impart a circular cross-section, circle with roughened edges, star, cross, polygon, triangle, crescent. The shape of the cross section can be varied by flow rate. For instance, if delivery is performed under variable speeds, a "beaded strand" formulation can be generated. Alternatively, a braided or collapsible metal or polymer mesh, hood or cone can be initially crimped within the catheter; upon reaching the site of the desired delivery, this can be deployed and expanded beyond the tip of the catheter to increase the effective diameter of the catheter and therefore the diameter of the formulation as it exits the catheter and the resulting coil. After the delivery of the foam, this mesh, hood or cone can be retracted back into the catheter for removal.

The surface properties of the coil may be controlled by: co-axial extrusion of a second material (e.g., protein) that coats or binds to the outer surface of the formulation as it is forming the coil; altering the pH locally while the surface reacts; or accelerating the reaction of the surface of the coil (e.g., catalyst). The surface properties of the coil may also be controlled by charge of the coil. The charge will partition to the exterior and can preferentially allow for protein binding to material surface. The surface properties of the coil may also be controlled by the surface energy of the formulation of polymer foam. Higher surface energy material with encourage adhesion and protein deposition on material surface.

The curvature of the coil may be controlled by altering the rate of extrusion of the formulation around the circumference of the catheter tip. For example, the inner lumen at the tip of the catheter may be roughened on one half of the circumference. This will reduce the velocity (and hence the flow rate) of the formulation on the roughened side of the catheter. The smaller amount of formulation on one half of the coil will cause the coil to curve in that direction. Greater degrees of relative flow will lead to more curvature of the extruded coil. This may be used to obtain a helical-like coil or coils that provide a multi-scale architecture. Curved coils may reduce the risk of embolism down collateral vessels because of this multi-scale architecture. A lower radius of curvature will result in a material more amenable to closepacking. This may result in greater efficacy by impeding flow more effectively.

Figure 5A:
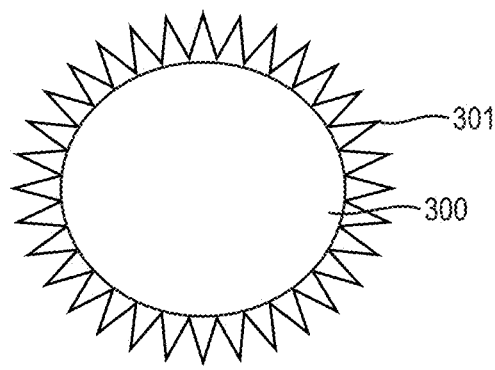
FIGS. 5A and 5B show a cross-sectional view of a coil with an in-situ forming coating, in accordance with embodiments of the present invention.
Figure 5B:
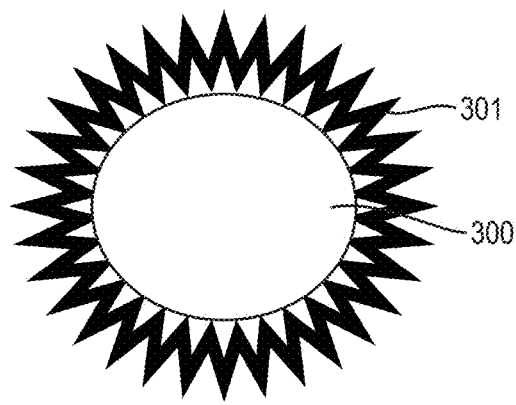

As shown schematically in cross-section in FIG. 5A, a pre-formed aneurysm coil 300 may be coated with a pre-polymer 301. As shown schematically in cross-section in FIG. 5B, the expanded aneurysm coil 300 foams upon deployment into an aqueous environment. For example, a platinum aneurysm coil is coated with expanding adherent formulations that effectively increase the diameter of the preformed coil once deployed into an aqueous or other environment. The increase in diameter can improve aneurysm fill and the compliant exterior can effectively mold together to eliminate interstitial gaps and stop flow within the aneurysm. The coating prepolymer can be a multifunctional moisture sensitive silane or a polyisocyanate prepolymer. The pre-polymer coating may be further coated with an outer, protective layer, preferably of a water soluble polymer (e.g., PEO). Alternately, a preformed coil may be coated with an in-situ foaming prepolymer or formulation simultaneously with its delivery to an aneurysm or other space in the body. The catheter through which the preformed coil is to be delivered is filled with the prepolymer or formulation prior to advancing the preformed coil through the catheter's lumen. Alternately, a specialized catheter may be used that has two concentric and coaxial lumens. The inner lumen is used to advance and deploy the preformed coil and the outer lumen is used to provide a pool or volume of prepolymer or formulation at the distal end to coat the preformed coil.

As shown in FIG. 6, the aneurysm coil 300 may be deployed into the aneurysm space 303 or space excluded by a stent graft 304 prior to, simultaneously with, or just after an in-situ forming foam 305 has been deployed into the space 303 to further seal the aneurysm.

Resistance of Blood Flow

Foams of the invention promote reduced blood flow when brought into contact with blood or sites of blood flow (e.g., Type II endoleaks). In preferred embodiments, foams of the invention have cell and pore structures with characteristics (including size, morphology, and tortuosity) that permit blood to enter the foam but which provide resistance to blood flow.

Pore density (defined as the number of open pores per unit area) can be controlled by adjusting the types and levels of ingredients in the formulation. In general, pore density can be altered by balancing the isocyanate index, surfactant levels, catalyst levels controlling both blowing and gelling rates, and the polyol viscosity. In many cases, subtle changes to a single ingredient level can drastically change the pore density.

In some cases, aneurysms continue to grow and remodel after placement of an endovascular graft. This growth can occur along the axis of the blood vessel leading to blood vessel dilatation at the proximal or distal ends which provided a seal against blood flow into the aneurysm sac. As this growth occurs, the seal may become compromised, the aneurysm sac pressurized and result in an increased risk of aneurysm rupture for the patient. The presence of the porous foam material in the aneurysm sac may lead to tissue ingrowth and ultimately stabilization of the aneurysm preventing aneurysm growth. For this purpose, the resulting in-situ foam preferably has an open cell structure and pore size conducive to tissue ingrowth (at least in the outer portion of the implant), and a resulting pore size preferably between 1 and 1000 microns and more preferably between 5 and 500 microns.

In some embodiments, a kit including one or more of the compositions previously discussed (e.g., a kit including a polymer formulation that can be foamed in-situ, a device comprising such a polymer formulation, a fluid for exposing to a polymer formulation to cause the foaming thereof and any other additive (e.g., external gas, second agent, etc.), a kit comprising a polymer formulation and a delivery system that can be used to create and/or deploy a polymer foam, or the like, is described. A "kit," as used herein, typically defines a package or an assembly including one or more of the compositions of the invention, and/or other compositions associated with the invention, for example, as previously described. In certain cases, some of the compositions may be constitutable or otherwise processable, for example, by the addition of a suitable solvent, other species, or source of energy (e.g., UV radiation), which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, fits, filters, rings, clamps, wraps, patches, containers, tapes, adhesives, and the like, for example, for using, administering, modifying, assembling, storing, packaging, preparing, mixing, diluting, and/or preserving the compositions components for a particular use, for example, to a sample and/or a subject.

A kit of the invention may, in certain cases, include different compositions that can be mixed to form a product. In certain embodiments, the kit may include physically separated chambers to hold the compositions, and a mechanism that is activated by a user or a machine for discharging the compositions and/or mixing them together. As a non-limiting example, the kit may include a dual barrel syringe having first and second chambers that contain first and second compositions, wherein the first and second chambers are physically separated, for example by a wall. In this example, the user may depress the plunger of the dual-barrel syringe to eject the first and second compositions from the first and second chambers. In certain embodiments, the kit also includes a static mixing nozzle, a dynamic mixing nozzle, an impeller, or a mixing chamber to permit the components to mix prior to or during discharge. In some embodiments, the kit includes a container or chamber within a delivery device that contains, or is configured to contain, saline or another fluid intended to cause the foaming reaction of the polymers delivered in accordance with the invention.

A kit of the present invention may, in some cases, include a preformed aneurysm coil or other medical device for use with the in-situ foaming formulation.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. In some cases, the instructions may also include instructions for the delivery and/or administration of the compositions, for example, for a particular use, e.g., to a sample and/or a subject, or to deliver the compositions of the invention into contact with bodily tissues to prevent, limit, or otherwise control bleeding or the flow of other bodily fluids. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

In the compositions of the invention, the term "alkyl" refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclochexyl, and the like.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, and the like.

The terms "alkenyl" and "alkynyl" refer to unsaturated aliphatic groups analogous in length and possible substitution to the alkyls described above, but that contain at least one double or triple bond respectively.

The terms "heteroalkenyl" and "heteroalkynyl" refer to unsaturated aliphatic groups analogous in length and possible substitution to the heteroalkyls described above, but that contain at least one double or triple bond respectively.

As used herein, the term "halogen" or "halide" designates —F, —Cl, —Br, or —I.

The terms "carboxyl group," "carbonyl group," and "acyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." The term "carboxylate" refers to an anionic carboxyl group. In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

The term "aryl" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups. In some cases, the The term "alkoxy" refers to the group, —O-alkyl.
The term "aryloxy" refers to the group, —O-aryl.
The term "acyloxy" refers to the group, —O-acyl.
The term "aralkyl" or "arylalkyl", as used herein, refers to an alkyl group substituted with an aryl group.

The terms "heteroaryl" refers to aryl groups comprising at least one heteroatom as a ring atom.

The term "heterocycle" refers to refer to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms. The term "heterocycle" may include heteroaryl groups, saturated heterocycles (e.g., cycloheteroalkyl) groups, or combinations thereof. The heterocycle may be a saturated molecule, or may comprise one or more double bonds. In some case, the heterocycle is a nitrogen heterocycle, wherein at least one ring comprises at least one nitrogen ring atom. The heterocycles may be fused to other rings to form a polycyclic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamnethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The terms "amine" and "amino" are art-recognized and refer to both unsubstituted and substituted amines, e.g., a moiety that can be represented by the 30 general formula: N(R')(R")(R''') wherein R', R", and R''' each independently represent a group permitted by the rules of valence. An example of a substituted amine is benzylamine.

Any of the above groups may be optionally substituted. As used herein, the term "substituted" is contemplated to include all permissible substituents of organic compounds, "permissible" being in the context of the chemical rules of valence known to those of ordinary skill in the art. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein, e.g., a drug or a peptide. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaruomatic moieties, —CF3, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like. The peptides described herein are inclusive of at least two amino acids connected by amide bond.

The present invention is further described with reference to the following non-limiting examples.

Example 1

A plastic cup was used to simulate an aneurysm with two 4 mm ID lumbar arteries (bottom) and one 6 mm ID IMA (top). Additionally, the model was operated under a static head of fluid pressure such that a flow rate of 40 ml/min out of the IMA and into the lumbar arteries was maintained. The material was delivered in <5 minutes to fill the 40 ml aneurysm via a 1.8 mm ID blunt tip.

During and after the delivery the material remained cohesive and remained in the target location, without embolizing the model collateral vessels. Within minutes after delivery was completed the material solidified in the interior and foamed forming a robust elastic foam.

Example 2

In this example, an in-situ forming foam demonstrated beneficial performance in an anatomically correct model. An anatomically correct model of a large human aortic aneurysm was made of molded silicone. The model had an aneurysm volume of 285 ml and a complex geometry. A bifurcated sent graft (36×20 mm) with a 16 mm extension was deployed in the model prior to injection of the material into the space between the graft and the aneurysm wall. The formulation delivered via a 4 mm catheter effectively filled 90+% of the space between the graft and the model without compromising the proximal or distal seal zones. The skin of the formulation impinged upon the graft but did not affect the diameter of the stent graft lumens and stayed within the aneurysm space without migrating into the collateral vessels. The formulation formed an elastic foam within minutes after deployment. This example demonstrates the benefits of lava-like foam characteristics in effectively and selectively filling aneurysm spaces and other bodily cavities. The quickly formed skin of the material maintains material cohesion while allowing the formulation to flow over and fill a complex 3D space.

Example 3

In this example, an isocyanate prepolymer formulation was coated with a siloxane based formulation and delivered through a coaxial delivery catheter. The two streams were not coaxial, but were attached to each other and delivered in parallel.

Example 4

A two-part lava form was created upon mixing of the two parts accompanied by contact with a biological environment. The biological environment accelerated the foam reaction at the surface, which resulted in a formation of a mechanically robust skin that limits material embolization. The mixing of the two components triggered a slower reaction that cured the interior of the foam. An example of this concept may be comprised of ethoxy functionalized siloxanes which react upon contact with water, and a tin catalyst. Furthermore, this example can include silicone hydrides that react with silanols in the presence of catalyst to generate gas creating a foam. A specific formulation composition to illustrate the two-part lava foam concept is shown below:

| Formulation component | Wt % |
| --- | --- |
| 1000 Cp silanol | 87.0% |
| 4 Cp Poly(diethoxysiloxane) | 5.0% |
| 30 Cp methylhydrosiloxane-dimethylsiloxane copolymer | 5.0% |
| Tin II Octoate (95%) | 3.0% |
| Tantalum powder | 24.0% |

As shown in FIG. 7, the formulation reacted quickly upon mixing and exposure to water resulting in a rubbery foam that filled cavity spaces of the model without extending into peripheral vessels. The material is seen to effectively fill model aneurysm spaces without extending into mock lumbar vessels located at the bottom of the model.

Example 5

A one-part lava form was created via a formation of a mechanically robust lava skin upon contact with biological environment. The interior of foam solidified more slowly than the exterior skin, thus allowing for continued deformation and expansion of the foam, which is beneficial for filling complex cavities. In a specific embodiment of this concept, the foam may be comprised of moisture-sensitive isocyonate functionalized siloxane. Such a siloxane reacted in the presence of water aided by a catalyst to form a robust foam. The foam first formed a viscous outer skin and subsequently solidified in its interior. A specific example of such a formulation that forms an embolization retarding outer skin is demonstrated in the table below:

| Formulation components | Wt % |
| --- | --- |
| 3500 Cp prepolymer | 95.0% |
| 1,8-Diazabicyclo[5.4.0]undec-7-ene | 5.0% |
| Tantalum powder | 15.0% |

Figure 8A:
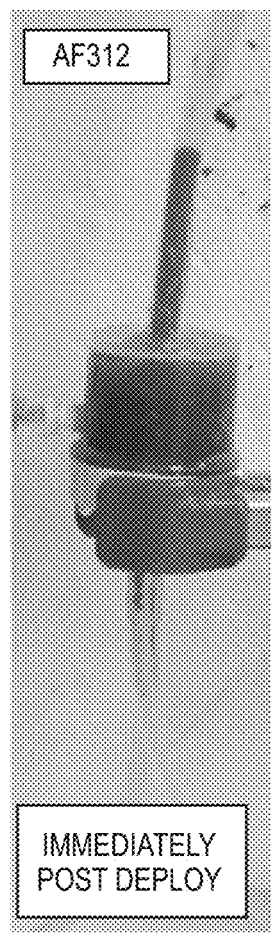
FIGS. 8A and 8B show the formation of lava-like foam from a one-part formulation.
Figure 8B:
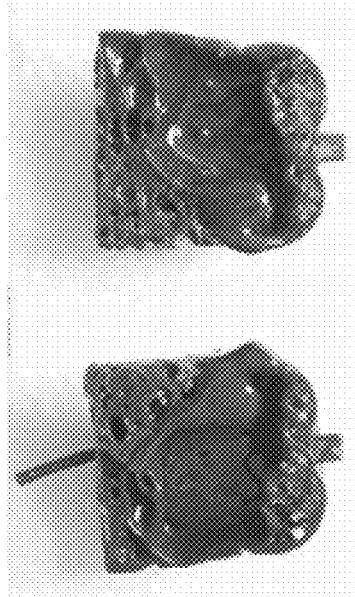

The formulation reacted quickly on the surface upon exposure to water, resulting in viscous outer skin. The resulting foam effectively filled cavity spaces in an aneurysm model without extending into peripheral vessels. Use of this material in an example model is shown in FIG. 8. The material is seen to effectively fill aneurysm spaces without extending into mock lumbar vessels 24 hours after the interior of the foam is completely solidified.

Example 6

A one-part formulation was provided as follows:

| Formulation component | Wt % |
| --- | --- |
| 1000 cP silanol | 79.9% |
| 3-isocyanotopropyltrimethoxysilane (95%) | 10.0% |
| Methyltriacetoxysilane (95%) | 10.0% |
| DBTDL | 0.1% |
| Tantalum powder | 12.0% |

Figure 9A:
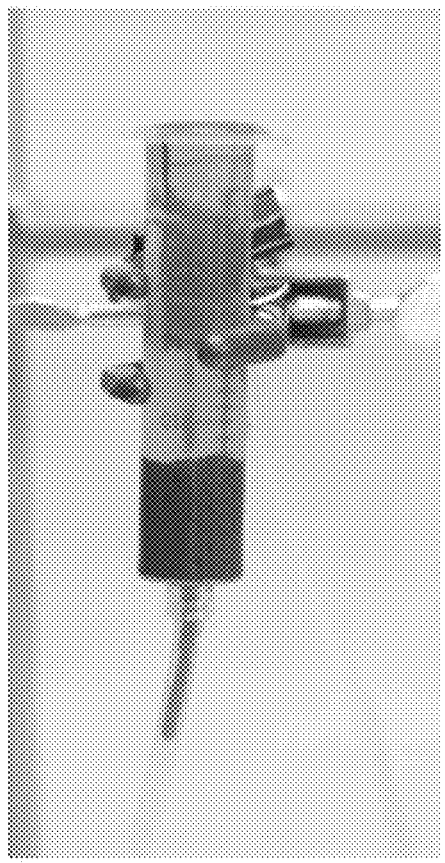
FIGS. 9A, 9B, and 9C show the formation of lava-like foam in a coil configuration from a one-part formulation.
Figure 9B:
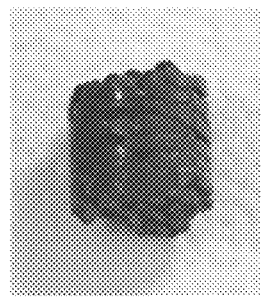
Figure 9C:
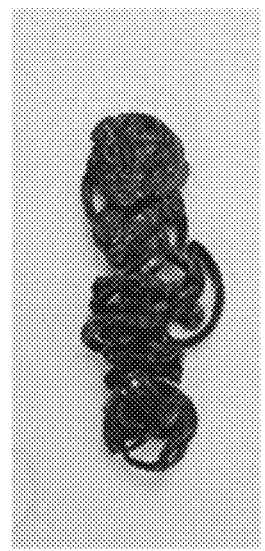

The formulation reacted quickly upon surface exposure to water, resulting in a coherent coil upon delivery through a thin catheter-like tube as shown in FIG. 9. The coil effectively packed to cavity spaces without extending into peripheral vessels in the aneurysm model shown in FIG. 9. The material is seen to effectively form a densely packing coil that effectively fills model aneurysm spaces without substantially extending into mock lumbar vessels located at the bottom of the model.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

What is claimed:

1. A method of treating an aneurysm in a patient, comprising the step of:
   delivering, within an aqueous space defined by an inner wall of the aneurysm and an outer wall of a medical device within the aneurysm, an in situ forming foam that comprises a polymer and reacts in the space to generate a gas and form a foam structure, which has a plurality of cells that contain said gas within a skin, and which is in conformal contact with tissue surrounding the space.

2. The method of claim 1, wherein the in situ forming foam is formed from a multi-functional silane.

3. The method of claim 2, wherein the multi-functional silane is formulated with tin.

4. The method of claim 2, wherein the multi-functional silane is formulated with titans.

5. The method of claim 2, wherein the in situ forming foam is formed by a reaction of the multi-functional silane and hydroxyl-containing siloxanes.

6. The method of claim 1, wherein the in situ forming foam is formed from a multi-functional isocyanate polymer.

7. The method of claim 1, wherein the medical device is a stent graft contacting first and second ends of the aneurysm.

8. The method of claim 1, wherein the step of delivering the in situ forming foam includes the steps of:
   inserting a distal end of a catheter into the space and flowing, through the catheter and into the space, said in situ forming foam.

9. The method of claim 1, wherein the in situ forming foam forms a coil within the space.

* * * * *